United States Patent [19]

Hannan et al.

[11] Patent Number: 4,513,280
[45] Date of Patent: Apr. 23, 1985

[54] METHOD AND APPARATUS FOR THE DETECTION OF TOXICANTS

[75] Inventors: Patrick J. Hannan, Washington, D.C.; Arthur V. Stiffey, Slidell, La.; N. Lynn Jarvis, Woodbridge; Henry Wohltjen, Burke, both of Va.

[73] Assignee: The United States of America as represented by the Secretary of the Navy, Washington, D.C.

[21] Appl. No.: 656,208

[22] Filed: Oct. 4, 1984

[51] Int. Cl.³ .................... G08B 17/10; C12Q 1/04
[52] U.S. Cl. .................... 340/632; 204/403; 204/433; 204/1 T; 324/438; 435/32; 435/34; 435/39; 435/40; 435/291; 435/315; 435/316
[58] Field of Search .................... 204/1 T, 415, 433; 435/32, 34, 39, 40, 287, 289, 291, 315, 316; 324/438; 340/632

[56] References Cited

U.S. PATENT DOCUMENTS

| | | | |
|---|---|---|---|
| 3,681,025 | 8/1972 | Dalgaard | 324/438 X |
| 3,743,581 | 7/1973 | Cady et al. | 435/34 |
| 3,944,471 | 3/1976 | Waters | 435/291 X |
| 4,036,698 | 7/1977 | Bush et al. | 435/34 X |
| 4,106,995 | 8/1978 | Petersen et al. | 435/315 X |
| 4,152,215 | 5/1979 | Yoshino et al. | 435/289 |
| 4,197,369 | 4/1980 | Weaver | 435/39 X |
| 4,326,200 | 4/1982 | Bushman | 340/632 |

Primary Examiner—G. L. Kaplan
Assistant Examiner—Nam X. Nguyen
Attorney, Agent, or Firm—Robert F. Beers; William T. Ellis

[57] ABSTRACT

A method and apparatus for rapidly detecting toxicants via the use of a first $CO_2$ sensing cell and a second reference $CO_2$ sensing cell, with each sensing cell including a first chamber and a second chamber, separated by a $CO_2$ permeable membrane, and a pH sensor disposed in each of the second chambers. The method includes the step of placing distilled water in the first chamber of each cell, and allowing its dissolved $CO_2$ to become equilibrated with the water in the second chamber, from which it is separated by the $CO_2$ permeable membrane. Next, exact amounts of a microorganism and sugar are added to small dishes in the first chambers along with control vegetation for one dish and vegetation to be tested to the other dish. Then the first chambers are completely filled with distilled water and the dishes are agitated to facilitate a solution of microorganisms and sugar. The method further includes the steps of sensing the pH in the liquid contained in each of the second chambers, determining the difference between the outputs from the pH sensors, and generating an alarm signal if this difference equals or exceeds a predetermined threshold. In one embodiment, yeast is utilized as the microorganism.

13 Claims, 4 Drawing Figures

TYPICAL OUTPUT DATA

METHOD AND APPARATUS FOR THE DETECTION OF TOXICANTS

BACKGROUND OF THE INVENTION

This invention relates generally to toxicant sensors, and more particularly to toxicant sensors which utilize living organisms.

Typically, toxicity measurements are based on the percentage of mortalities of a population of organisms resulting from exposure to a given concentration of test compound. Alterations in growth rate are also studied, and the length of the test generally is determined by the time required for measurable growth to take place. This time could range from hours to days and would require measurement of biomass or cell numbers.

Another technique for measuring and detecting toxicants involves the use of luminescent organisms such as the marine dinoflagellates. Here, the light intensity given off by such organisms changes according to ambient conditions. Thus, the above mentioned light intensity may be monitored to detect the presence of toxicants which could affect it.

These prior art designs are relatively bulky, require significant time to obtain measurable microorganism growth change, and in some cases require the use of exotic microorganisms.

OBJECTS OF THE INVENTION

Accordingly, it is an object of the present invention to provide an on-site biological sensor for the detection of toxicants.

It is a further object of the present invention to provide a biological sensor capable of rapid detection of toxicants.

It is yet a further object of the present invention to provide a small, low cost biological toxicant sensor which utilizes microorganisms with a fast growth rate.

It is a further obJect of the present invention to measure the growth rate of microorganisms to a toxicant without measuring biomass or cell numbers of the microorganisms.

Other obJects, advantages, and novel features of the present invention will become apparent from the detailed description of the invention, which follows the summary.

SUMMARY OF THE INVENTION

Briefly, the above and other objects are achieved by a biological sensor for the detection of toxicants in a sample comprising a flush reservoir for containing a liquid flush medium, a first and second $CO_2$ sensing cells, each sensing cell including a first chamber for holding a mixture of a nutrient and microorganisms in the liquid flush medium, a second chamber containing the liquid flush medium, a $CO_2$ permeable membrane disposed to separate the first and second chambers, and a pH sensor disposed in the second chamber. The device further includes means in one first chamber for holding microorganisms and a growth medium, and a sample to be tested for toxicants. The other first chamber also includes means for holding microorganisms, a growth medium and a control item. The $CO_2$ produced by the microorganisms in the growth medium contained in the first chambers of the first and second $CO_2$ sensing cells is passed through the $CO_2$ permeable membrane into the second chambers of the first and second $CO_2$ sensing cells containing the pH sensors. The device further comprises means for determining the outputs from the pH sensors in the first and second $CO_2$ sensing cells and generating an alarm signal if the difference equals or exceeds a predetermined threshold.

In a preferred embodiment, the liquid flush medium is distilled water provided from a reservoir as a means of dissolving the nutrients and suspending the microorganisms in the first chamnbers. It is also used to flush out the sensor between uses. The microorganism contained in the microorganism medium may be yeast.

DETAILED DESCRIPTION OF THE PREFERRED EMBODIMENT

The present invention comprises a small, low cost, onsite biological apparatus for detecting the presence of toxicants. The presence of the toxicants is determined by their effect on the $CO_2$ production of the test microorganisms.

Figure 1:
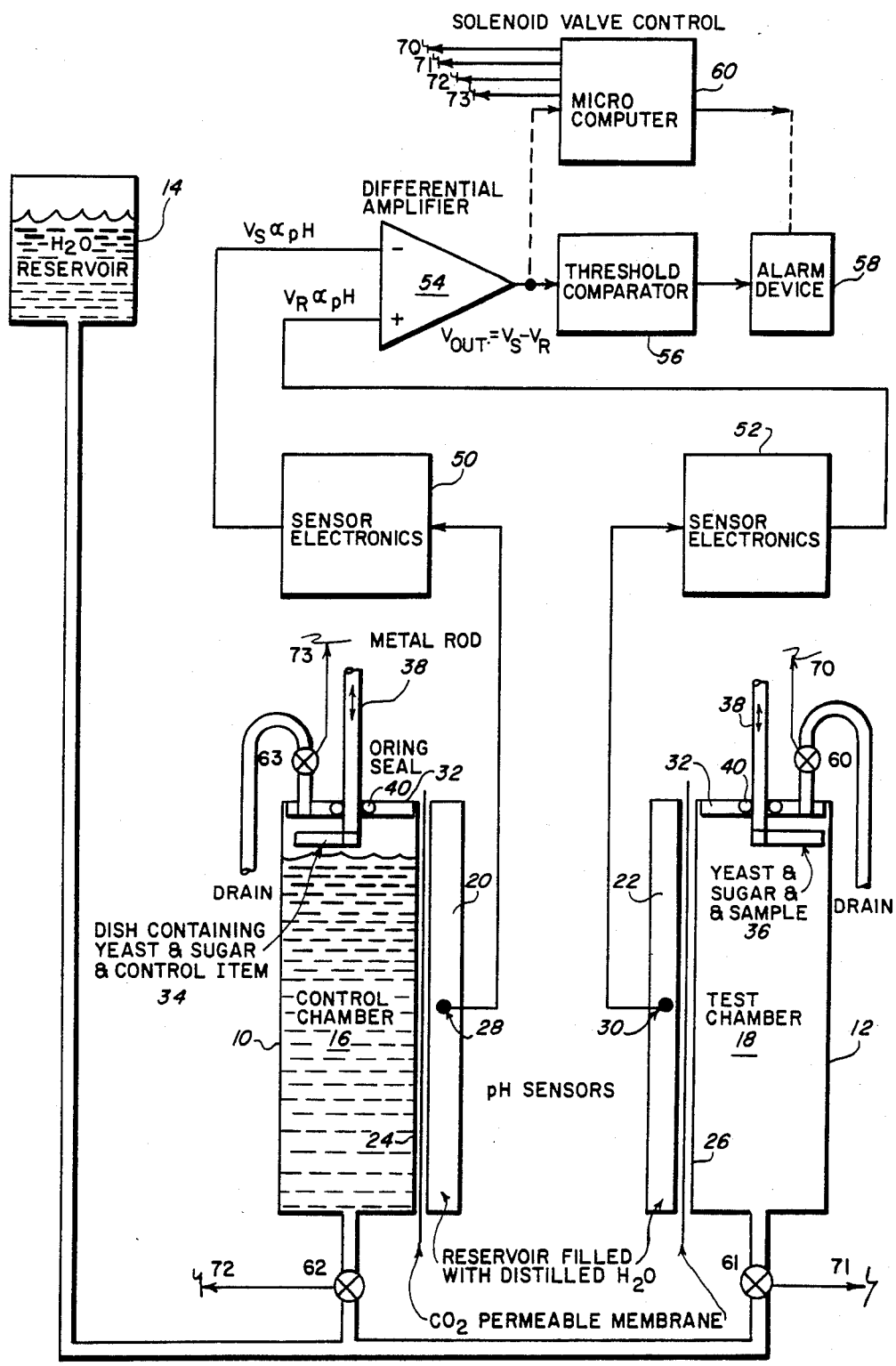
FIG. 1 is a schematic block diagram of one embodiment of the present invention. Note that the elements in the figure are not drawn to scale.

Referring now to FIG. 1, parallel detector cells 10 and 12 are shown connected to a distilled water reservoir 14 by means of a set of valves. The detector cell 10, marked "Control", detects the $CO_2$ production of a microorganism population which has not been exposed to a toxicant. The detector cell 12, marked "Test", detects the $CO_2$ production of a microorganism population containing a toxicant. The two cells 10 and 12 may be identical in construction. Each detector cell includes a first chamber (16, 18) for holding a mixture of the microorganisms and a liquid nutrient, a second chamber (20, 22) containing distilled water, a $CO_2$ permeable membrane (14, 26) disposed to separate the first and second chambers, and a pH sensor (28, 30) disposed in the second chamber for sensing the pH thereof.

In operation, the top segment 32 of each detector cell (10, 12) is removed from the assembly to allow the placement of known amounts of a growth medium such as sugar and a microorganism such as dried yeast in a rectangular dish (34, 36) attached to a metal rod 38 extending through an O-ring seal 40. In the dish 36 of the "Test" cell 18 is added a sample of vegetation suspected to contain a toxicant, and to the "Control" dish 34 is added a similar volume of vegetation believed to be free of toxicant. Once the top segment 32 of each detector cell has been joined to the unit, and with the rectangular dish of each raised to the highest level within the first chambers 16 and 18, a flush medium such as distilled water is allowed to flow in to each unit from the reservoir 14 until almost to the level of the rectangular dish. A short time is then 10 allowed for $CO_2$ equilibrium to be established between the water in the first and second chambers. Then additional distilled water is allowed to flow in the chambers until the water extends into the opening of the drain valves in the top segments 32. The drain valves are then closed. Mixing of the yeast, sample or control vegetation, and water is then provided by sliding up and down the rods extending through the O-ring seals. As $CO_2$ is evolved by the yeast and the $CO_2$ permeates through the $CO_2$ permeable membranes 24 and 26, there follows a drop in pH of the water contained in the second chamber (20, 22) of each cell; if the rate of change of the "Test" cell 18 is sufficiently different than that of the "Control" cell 10, a comparison circuit causes an alarm to ring.

There are a variety of pH sensors available on the market for sensing this increase in the hydrogen ion concentration. For example, a conventional glass pH sensor may be utilized to sense the pH of the distilled water in the second chambers. A second example of such a pH sensor is the CHEMFET, which is an ion sensitive FET with a pH sensitive membrane disposed over the gate region. See as a reference the book "Ion Selective Electrodes in Analytical Chemistry" edited by Henry Freiser, Plenum Press, New York, N.Y., Vol. 2, 1980.

It should be noted that there are a variety of microorganisms which could be utilized to implement the present toxicant sensor. The microorganism chosen will depend on the toxicant to be detected. Such a microorganism should have the characteristics of being relatively low cost, and having a fast growth rate which is suitable for a quick detection capability. Such a microorganism which has the above noted characteristics and can be used to detect a wide variety of toxicants is yeast. There are a wide variety of yeast strains which could be utilized in the present system. By way of example, the yeast strain *Saccharomyces cerevisiae* could be utilized in the present design. It should be noted that yeast strains are especially suitable for detecting Yellow Rain compounds of the type dispensed in military application.

The $CO_2$ generated by the yeast has a more appreciable effect on the pH of a small volume rather than a large one. A width of 3 cm, a height of 8 cm, and a depth of 0.8 cm would provide sufficient volume (approximately 2 ml) for the first chamber. This volume is large enough, however, for the introduction of a leaf specimen. Because the rectangular dish would occupy most of the space between the front and back surfaces of the chamber, movement of the dish up and down in the distilled water would provide rapid mixing, and quick dissolution, of the yeast and sugar.

The use of a $CO_2$ permeable membrane (24, 26) between the first and second chambers is advantageous in preventing direct contact between the pH sensor and the sample to be tested. Such direct contact should be avoided because the the sample itself may affect the pH. Accordingly, the pH of the sample could cause a differential pH reading between the "Test" $CO_2$ sensor cell and the "Control" $CO_2$ sensor which would thus provide a false toxicant detection reading. This $CO_2$ permeable membrane may be dimethyl silicone or silane rubber.

Following an experiment of the type described, the system would be flushed with distilled water from the reservoir. Removal of the top section would provide access to the interior of the cell and facilitate cleaning of the interior surfaces of all residues of yeast before the next test. Distilled water is then introduced into the first chamber and an equilibrium between this water and the water in the second chamber is established, thereby reducing the dissolved $CO_2$ content of the second chamber. Repeated rinsings will result in a low concentration of dissolved $CO_2$, suitable for the start of the next test.

In a preferred embodiment, the pH sensors convert the pH acidity indication into electrical signals. These electrical signals are then compared and a difference electrical signal is generated. In the embodiment shown in FIG. 1, sensor electronics 50 and 52 are provided at the electrical outputs of the pH sensors 28 and 30, respectively. The specific type of sensor electronics to be utilized depends on the type of pH sensor used in the device. For example, for a conventional glass pH sensor, a standard operational amplifier circuit may be utilized to provide impedance buffering for the pH electrode circuits. Likewise, for a CHEMFET pH sensor, a standard amplifying circuit may be utilized.

The difference between the voltage $V_s$ generated by the pH sensor 52 and the voltage $V_r$ generated by the pH sensor 50 can be obtained with a variety of comparison circuits. By way of example, a differential amplfier 54 could be utilized to provide the difference voltage $V_{out}$. In the implementation shown in FIG. 1, the output from the sensor electronics 52 for the pH sensor 30 is applied to the positive terminal of the differential amplifier 54 while the output from the sensor electronics 50 for the pH sensor 28 is applied to the negative input of the amplifier 54.

The output from the differential amplifier 54 may then be utilized to generate an alarm signal if the difference voltage equals or exceeds a predetermined threshold voltage. This threshold comparison function could be implemented simply by attaching a threshold comparator 56 to the differential amplifier 54, and then applying the threshold comparator 56 output directly to an alarm device, light indicator, or a digital readout device for reading out the magnitude of the voltage $V_{out}$. Such an alarm device is represented in FIG. 1 by the alarm block 58.

In one embodiment of the present invention, a computer device 60 may be utilized to compare the voltage $V_{out}$ to a threshold voltage and then to generate an alarm signal if the voltage $V_{out}$ equals or exceeds the threshold. By way of example, the computer 60 could be implemented simply by an Apple microcomputer Model 2E. The computer 60 could be utilized to record the differential voltage output $V_{out}$ over a period of time, such as 15 minutes, and then could be programmed to utilize the voltage $V_{out}$ at this 15 minute point to control the alarm device 58. Likewise, the computer 60 could be utilized to periodically sample the volta $V_{out}$ over a given time interval and then sum all of these sample voltages and compare this voltage sum to a threshold, or divide this voltage sum by the number of sample points and compare it to a threshold voltage. This data averaging would provide greater resolution and greater reliability in the statistical validity of the date.

Additionally, the computer 60 could be utilized to generate control signals on the lines 70, 71, 72, and 73 to control solenoid valves 60, 61, 62 and 63, respectively. The sequence of openings and closings of the valves 60, 61, 62 and 63 could be implemented in the computer 60 simply by means of a clock and a timing sequence. One programming sequence that may be utilized is as follows.

1. The rectangular dishes in the test and control chambers are removed and supplied with yeast and sugar.

2. The rectangular dish of the test chamber is supplied with a sample to be analyzed and the rectangular dish in the control chamber is supplied with a control item.

3. The dishes are placed into the chambers, the chambers are closed, and the dishes are withdrawn to the tops of the chambers.

4. Valves 60, 61, 62 and 63 are opened to allow water to fill the chambers to a point just below the dishes. The valves are then closed.

5. The system is allowed to stand until stable pH readings are obtained from both test and control pH sensors.

6. Valves 60, 61, 62 and 63 are opened to completely fill the chambers.

7. The dishes are agitated up and down to mix the water, yeast, sugar and sample or control item.

8. The difference between the voltages generated by the pH sensors 28 and 30 is determined and compared to a threshold voltage. As noted previously a summed set of voltage samples may be compared to a threshold, or the average of a summed set of voltage samples may be compared to a threshold, or a voltage difference sample taken after a second predetermined period of time may be compared to a threshold voltage.

9. An alarm signal is generated if the voltage difference in the comparison of step 8 equals or exceeds the threshold voltage.

10. After the toxicant testing has been completed, the entire system is purged by purging the first chambers of the $CO_2$ sensor cells with distilled water. This purging is accomplished by opening valves 61 and 62 to the distilled water reservoir and the valves 60 and 63 for the drain. As noted previously, this flushing of distilled water will take place such that a number of times the volume of the chambers 16 and 18 is flushed out through the valves. The tops of the first chambers may also be removed to wipe the sides of the first chambers. The foregoing programming sequence is simple in execution and is controlled simply by a clock.

Figure 2A:
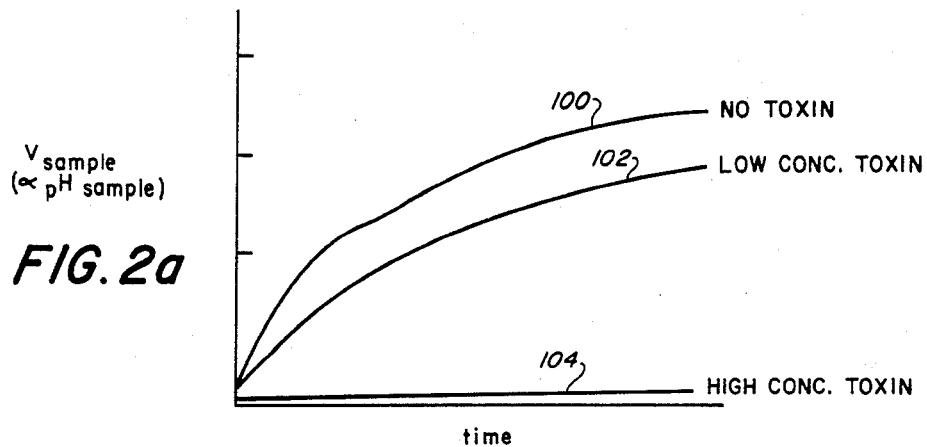
FIG. 2a is a graph showing the voltage response from the sample detector cell for a high concentration toxicant, a low concentration toxicant and no toxicant.
Figure 2B:
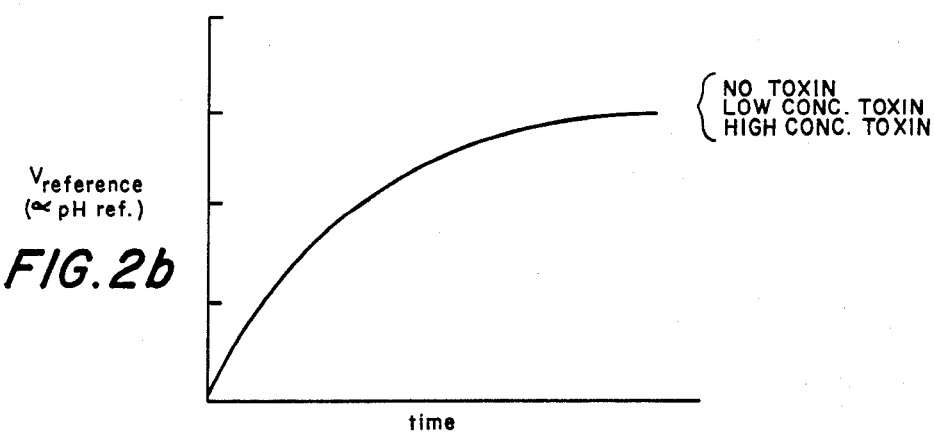
FIG. 2b is a graph showing the voltage response from the reference detector cell.
Figure 2C:
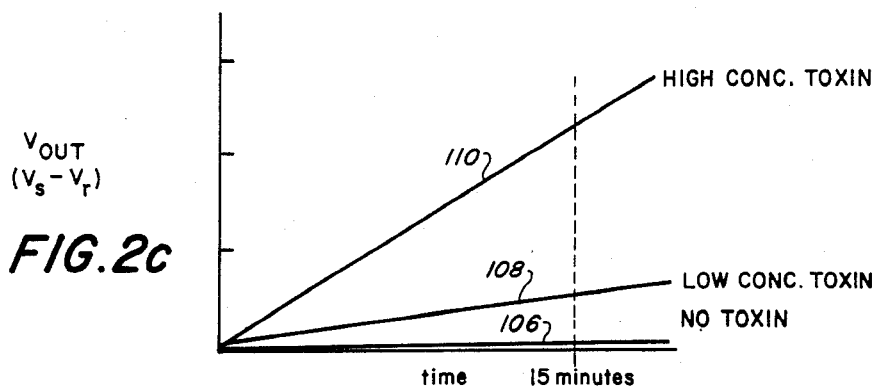
FIG. 2c is a graph showing the voltage difference output between the sample detector cell and the reference detector cell for a high concentration toxin, a low concentration toxin and no toxin.

FIG. 2a represents typical voltage output data versus time for the pH sensor of the sample $CO_2$ sensor cell for the no toxin situation (curve 100), the low concentration toxin siutation (curve 102), and the high concentration toxin situation (curve 104). FIG. 2b represents the reference voltage output $V_r$ versus time. FIG. 2c represents the difference voltage output $V_{out}$ versus time for the no toxin situation (curve 106), the low concentration toxin situation (curve 108), and the high concentration toxin situation (curve 110).

It should be noted that the pH sensing which is performed in the second chambers could be accomplished by utilizing a pH indicator dye in the distilled water in those chambers. However, such a pH indicator configuration is not as sensitive as the device set forth in FIG. 1, and would be difficult to obtain an electronic readout therefrom. Alternatively, the pH sensor could be implemented by an optical fiber core (the bare core glass with the cladding removed) with a pH dye coated along the length thereof. This optical fiber pH sensor would then be disposed in the distilled water in the second chambers 20 and 22 along with a light emitting diode. Light from the light emitting diode would propagate in the optical fiber core disposed in the second chambers 20 and 22 to a photodetector disposed external to the chamber. As the pH of the distilled water in the second chambers changes in response to the diffusion of $CO_2$ therein, the color of the PH dye disposed over the optical fiber core will change. Accordingly, the light that is lost from the optical fiber core into the distilled water will depend on the dye color which is, in turn, dependent on the pH of the distilled water. Accordingly, the amount of light detected by the photodetector will be proportional to the pH of the distilled water in the second chambers 20 and 22.

The above described system provides a design for the rapid screening of potential toxicants that can be performed on-site. The design measures the response of a population of microorganisms exposed to a sample compound in comparison to a reference. A plurality of samples may be taken over a period of time, or a single sample may be taken after an arbitrary waiting period (e.g., 15 minutes). If the difference in the pH readings between the reference sensor cell and the sample sensor cell is large enough to suggest that the microorganism has been poisoned in the sample cell, then an alarm is sounded. The arbitrary waiting time to be utilized in the sampling sequence will depend on the concentration of the toxin, the sensitivity of the microorganism to the expected toxin, the voltage fluctuations at the output of the sensors, and the magnitude of the difference voltage required for an unambiguous identification of the toxin. It should be noted that very low concentration levels of toxin may require significantly longer waiting periods in order to effect a detection thereof.

It should be noted that the present design may essentially be considered a closed design which excludes air. The advantage to excluding air is that it prevents the $CO_2$ in the air from effecting the pH in the $CO_2$ sensing cells.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A biological sensor for the detection of toxicants in a sample comprising:

a first and second $CO_2$ sensing cells, each sensing cell including a first chamber for holding a liquid flush medium, a second chamber containing said liquid flush medium, a $CO_2$ permeable membrane disposed to separate said first and second chambers, and a pH sensor disposed in said second chamber, said first chamber of said first $CO_2$ sensing cell including means adaptable for agitation for holding microorganisms, a growth medium, and a control item, said first chamber of said second $CO_2$ sensing cell including means adaptable for agitation for holding microorganisms, a growth medium, and a sample to be tested for toxicants;

a flush reservoir for containing said liquid flush medium for connection to said first chambers of said first and second $CO_2$ sensing cells;

wherein the $CO_2$ produced by said microorganisms from the mixture of said microorganisms and said growth medium in said flush medium contained in said first chambers of said first and second $CO_2$ sensing cells is passed through said $CO_2$ permeable membrane into said second chambers of said first and second $CO_2$ sensing cells containing said pH sensors; and means for determining the difference between the outputs from said pH sensors in said first and second $CO_2$ sensing cells and generating an alarm signal if said difference equals or exceeds a predetermined threshold.

2. A biological sensor as defined in claim 1, wherein said liquid flush medium contained in said flush reservoir and in said first and second chambers of said $CO_2$ sensing cells is distilled water.

3. A biological sensor as defined in claim 2, wherein said holding means comprise:
a dish for holding said microorganisms, growth medium, and either the sample or the control item; and
means connected to said dish and extending externally of said first chamber to permit agitation of said dish.

4. A biological sensor as defined in claim 3, wherein said agitation means each comprise a rod connected at one end to said dish and extending out through the top wall of said first chamber, and adapted to hold said dish near the top of said first chamber and to agitate said dish.

5. A biological sensor as defined in claim 3, wherein said pH sensors produce an electrical signal proportional to the pH.

6. biological sensor as defined in claim 5 wherein said microorganism is yeast.

7. A biological sensor as defined in claim 6, wherein said $CO_2$ permeable membrane is dimethyl silicone.

8. A biological sensor as defined in claim 6, wherein said $CO_2$ permeable membrane is silane rubber.

9. A biological sensor as defined in claim 6, wherein said pH sensor is a pH electrode.

10. A biological method for detecting toxicants in a sample via the use of a first and second $CO_2$ sensing cells, with each $CO_2$ sensing cell including a first chamber and a second chamber, separated by a $CO_2$ permeable membrane, and a pH sensor disposed in a liquid in each of said second chambers, the method comprising the steps of:
disposing microorganisms, a growth medium for said microorganisms, and a sample to be tested for toxicants in said first chamber of said first $CO_2$ sensing cell along with a flush medium, while disposing microorganisms, a growth medium for said microorganisms, and a control item said first chamber for said second $CO_2$ sensing cell along with a flush medium;
agitating the contents of said first chambers;
sensing the pH in the liquid contained in each of said second chambers;
determining the difference between the outputs from said pH sensors; and
generating an alarm signal if said difference equals or exceeds a predetermined threshold.

11. A method as defined in claim 10, wherein said disposing step includes the steps of:
disposing said microorganisms, said growth medium and said sample in said first chamber of said first $CO_2$ sensing cell and disposing said microorganisms, said growth medium and said control item in said first chamber of said second $CO_2$ sensing cell at a location near the top of the respective first chambers;
flowing a flush medium of distilled water into said first chambers to a point just below the location of said microorganisms, growth medium, and either sample or control item;
permitting said distilled water to stand until approximately stable pH readings are obtained from said pH sensor in each of said second chambers of said $CO_2$ sensing cells; and completely filling said first chambers with said distilled water flush medium.

12. A method as defined in claim 11, wherein said disposing step comprises the step of disposing the microorganism yeast and the growth medium sugar in said first chambers of said $CO_2$ sensing cells.

13. A method as defined in claim 12, wherein said agitating step comprises the step of moving said microorganisms, said growth medium and said sample in one first chamber and moving said microorganisms, said growth medium, and said control item in the other first chamber in an up and down motion in said distilled water flush medium to promote mixing.

* * * * *